United States Patent
Karimirad et al.

(10) Patent No.: US 11,614,424 B2
(45) Date of Patent: Mar. 28, 2023

(54) NANOPORE DEVICE AND METHODS OF BIOSYNTHESIS USING SAME

(71) Applicant: PALOGEN, INC., Palo Alto, CA (US)

(72) Inventors: Bita Karimirad, Suwon (KR); Kyung Joon Han, Palo Alto, CA (US)

(73) Assignee: PALOGEN, INC., Palo Alto, CA (US)

( * ) Notice: Subject to any disclaimer, the term of this patent is extended or adjusted under 35 U.S.C. 154(b) by 434 days.

(21) Appl. No.: 16/832,990

(22) Filed: Mar. 27, 2020

(65) Prior Publication Data

US 2020/0348260 A1 Nov. 5, 2020

Related U.S. Application Data

(60) Provisional application No. 62/826,897, filed on Mar. 29, 2019.

(51) Int. Cl.
| | | |
|---|---|---|
| *B01J 19/00* | (2006.01) | |
| *G01N 27/447* | (2006.01) | |
| *B01L 3/00* | (2006.01) | |
| *G01N 33/487* | (2006.01) | |

(52) U.S. Cl.
CPC .... *G01N 27/44791* (2013.01); *B01J 19/0046* (2013.01); *B01L 3/502761* (2013.01); *G01N 33/48721* (2013.01); *B01J 2219/00572* (2013.01); *B01J 2219/00585* (2013.01); *B01J 2219/00639* (2013.01); *B01J 2219/00675* (2013.01); *B01J 2219/00713* (2013.01); *B01J 2219/00722* (2013.01); *B01L 2200/0663* (2013.01); *B01L 2300/0816* (2013.01); *B01L 2300/0896* (2013.01); *B01L 2400/0421* (2013.01); *B01L 2400/0424* (2013.01)

(58) Field of Classification Search
None
See application file for complete search history.

(56) References Cited

U.S. PATENT DOCUMENTS

2006/0046262 A1    3/2006  Mauritz

FOREIGN PATENT DOCUMENTS

| WO | WO 03/020415 | 3/2003 |
| WO | WO 2017/151680 | 9/2017 |
| WO | WO 2017/184677 | 10/2017 |

OTHER PUBLICATIONS

PCT International Search Report and Written Opinion for International Appln. No. PCT/US2020/025530, Applicant Palogen, Inc., dated Jun. 22, 2020 (13 pages).

*Primary Examiner* — Christopher M Gross
(74) *Attorney, Agent, or Firm* — Vista IP Law Group LLP

(57) ABSTRACT

A method of synthesizing an oligonucleotide using a nanofluidic device including a plurality of nanopore channels, a plurality of electrodes, and an electrolyte solution, includes coupling a primer to an inner wall of a nanopore channel of the plurality of nanopore channels, the primer having a protecting group. The method also includes applying a voltage to an electrode of the plurality of electrodes that corresponds to the nanopore channel to produce an acid from the electrolyte solution at the electrode. The electrode includes an anode and a cathode disposed at opposite sides of the nanopore channel. The method further includes the acid removing the protecting group from the primer. Moreover, the method includes coupling a nucleotide to the primer with the protecting group removed to form an intermediate product. In addition, the method includes repeating the steps on the intermediate product until the oligonucleotide is synthesized.

20 Claims, 11 Drawing Sheets

NANOPORE DEVICE AND METHODS OF BIOSYNTHESIS USING SAME

CROSS-REFERENCE TO RELATED APPLICATION

This application claims priority to U.S. Provisional Application No. 62/826,897, filed on Mar. 29, 2019 and, entitled "NANOPORE DEVICE AND METHODS OF BIOSYNTHESIS USING SAME," the contents of which are hereby expressly and fully incorporated by reference in their entirety, as though set forth in full. This application includes subject matter similar to the subject matter described in co-owned U.S. Provisional Patent Application Ser. No. 62/566,313, filed on Sep. 29, 2017 and entitled "MANUFACTURE OF THREE DIMENSIONAL NANOPORE DEVICE"; U.S. Provisional Patent Application Ser. No. 62/593,840, filed on Dec. 1, 2017 and entitled "NANOPORE DEVICE AND METHOD OF MANUFACTURING SAME"; U.S. Provisional Patent Application Ser. No. 62/612,534, filed on Dec. 31, 2017 and entitled "NANOPORE DEVICE AND METHODS OF ELECTRICAL ARRAY ADDRESSING AND SENSING"; U.S. Provisional Patent Application Ser. No. 62/628,214, filed on Feb. 8, 2018 and entitled "BIOMEMORY FOR NANOPORE DEVICE AND METHODS OF MANUFACTURING SAME"; U.S. Provisional Patent Application Ser. No. 62/711,234, filed on Jul. 27, 2018 and entitled "NANOPORE DEVICE AND METHODS OF DETECTING CHARGED PARTICLES USING SAME"; U.S. Utility patent application Ser. No. 16/147,362, filed on Sep. 26, 2018 and entitled "NANOPORE DEVICE AND METHOD OF MANUFACTURING SAME"; U.S. Utility patent application Ser. No. 16/237,570, filed on Dec. 31, 2018 and entitled "NANOPORE DEVICE AND METHODS OF ELECTRICAL ARRAY ADDRESSING AND SENSING"; U.S. Provisional Patent Application Ser. No. 62/802,459, filed on Feb. 7, 2019 and entitled "BIOMEMORY FOR NANOPORE DEVICE AND METHODS OF MANUFACTURING SAME"; U.S. Utility patent application Ser. No. 16/524,033, filed on Jul. 27, 2019 and entitled "NANOPORE DEVICE AND METHODS OF DETECING CHARGED PARTICLES USING SAME"; and U.S. Provisional Patent Application Ser. No. 62/971,104, filed on Feb. 6, 2020 and entitled "BIOMEMORY FOR NANOPORE DEVICE AND METHODS OF MANUFACTURING SAME." The contents of the above-mentioned applications are fully incorporated herein by reference as though set forth in full.

FIELD OF THE INVENTION

The present invention relates generally to nanofluidic systems, devices, and processes for synthesis of biopolymer molecules using the three dimensional ("3D") nanofluidic array devices and systems.

BACKGROUND

Two dimensional ("2D") microarrays can be used to examine/screen biological materials with high throughput, parallel, multiplex methods. Such a 2D microarray can include relatively short (e.g., 10s to 100s of base pairs) fragments of DNA ("tests" or "probes") linked to a solid substrate of the 2D microarray. Each test/probe can be a small portion of the gene. Biological molecules other than DNA fragments can likewise be utilized as tests/probes for hybridization with target RNA or cDNA. Identification and quantification of targets corresponding to the tests/probes can be achieved by measurement of fluorescence (e.g., target nucleic acids labeled tagged with fluorophores) or luminescence (e.g., target nucleic acids labeled with chemiluminescent materials).

3D nanofluidic array sensors are described in U.S. Provisional Patent Application Ser. Nos. 62/566,313, 62/593,840, 62/612,534, 62/628,214, 62/711,234, 16/147,362, 16/237,570, and 62/802,459, the contents of which have been previously incorporated by reference herein. 3D nanofluidic array sensors can identify numerous diverse genomic issues at various stages in human development using multiplexing, control, sensitivity, and specify at the nanoscale. 3D nanofluidic array sensors also minimize the form factor for clinical, scientific, and industrial applications as well as portable applications. In addition, a smaller form factor allows Lab-on-a-Chip applications, which can function as central components of clinical sensors (e.g., in micro-electro-mechanical system "MEMS" frameworks). These arrays and techniques using same facilitate rapid and effective genomic issue discovery strategies (e.g., using information from sequenced human genomes) utilizing specific targets (e.g., corresponding to various cancers).

A current nanofluidic device, also called a nanopore device, includes an array of nanometer range pores, each pore having a narrow channel hole (e.g., with a diameter of about 1 nm to about 1000 nm) that can accommodate and direct the flow of charged particles (e.g., ions, molecules, etc.) through the hole by the change in the ionic current and/or tunneling current. Because the phosphate backbone of a nucleic acid (e.g., adenine, cytosine, guanine, thymine in DNA, uracil in RNA) includes negatively charged oxygen molecules, nucleic acids will flow toward positively charged anodes. Similarly, hydrogen ("acid") ions formed at anodes will flow toward the negatively charged cathodes.

FIG. 1 schematically depicts a state-of-art solid-state based 2D nanopore sequencing device 100. While, the device 100 is referred to as "two dimensional," the device 100 has some thickness along the Z axis. In order to address the drawbacks (e.g., sensitivity, high translocation speed, electrical addressing, biomemory limitations, and manufacturing cost) of current state-of-art nanopore technologies, multi-channel nanopore array which allows parallel processing of biomolecule sequencing may be used to achieve label-free, amplification-free, and rapid sequencing. Examples of such multi-channel nanopore arrays are described in U.S. patent application Ser. Nos. 62/566,313, 62/593,840, 62/612,534, 62/628,214, 62/711,234, 16/147,362, 16/237,570, and 62/802,459, the contents of which have been previously incorporated by reference.

Various biological techniques require synthesized DNA molecules (e.g., as tests/probes). Current synthesizing devices can synthesize a variety of different biomolecules in a matter of hours. With advancements in semiconductor manufacturing technologies, solid-state nanopores have become an inexpensive and superior alternative to biological nanopores partly due to the superior mechanical, chemical and thermal characteristics, and compatibility with semiconductor technology allowing the integration into various nanodevices. However, current biosynthesis systems having only been miniaturized to the microarray level described above, and do not include nanopore technology. There is a need for biomolecule synthesis systems and methods with increased speed and flexibility (e.g., number of different molecules that can be synthesized simultaneously), and reduced cost and form factor. There is also a need for biomolecule synthesis systems and methods with more efficient and effective use of multi-channel nanofluidic arrays to achieve low cost and high throughput biomolecule synthesis with plug and play capability, and scalability. Further, there is a need for nanofluidic based biosynthesis systems and methods that address the shortcomings of currently-available biosynthesis configurations.

SUMMARY

Embodiments are directed to nanopore based biosynthesis systems and methods. In particular, the embodiments are directed to nanofluidic arrays (2D or 3D) for synthesizing biomolecules and methods for using same to synthesize biomolecules.

In one embodiment, a method of synthesizing an oligonucleotide using a nanofluidic device including a plurality of nanopore channels, a plurality of electrodes, and an electrolyte solution in the plurality of nanopore channel and in electrical contact with the plurality of electrodes, the method includes a. coupling a primer to an inner wall of a nanopore channel of the plurality of nanopore channels, the primer having a protecting group. The method also includes b. applying a voltage to an electrode of the plurality of electrodes that corresponds to the nanopore channel to produce an acid from the electrolyte solution at the electrode. The electrode includes an anode and a cathode disposed at opposite sides of the nanopore channel. The method further includes c. the acid removing the protecting group from the primer. Moreover, the method includes d. coupling a nucleotide to the primer with the protecting group removed to form an intermediate product. In addition, the method includes e. repeating steps b. to d. on the intermediate product until the oligonucleotide is synthesized.

In one or more embodiments, coupling the primer to the inner wall of the nanopore channel includes coupling a dress polymer to the inner wall of the nanopore channel and couple the primer to the dress polymer. The dress polymer may be selected from the group consisting of polyethylene glycol (PEG 5000) monomethyl ester, poly(ortho esters), aliphatic polyester, temperature resistant polymers, aliphatic homopolymers, polycaprolactons, polymers with cosolvents, b polar polymers, hydrophilic polymers, and hydrophobic polymers. The protecting group may include dimethoxytrityl ("DMT").

In one or more embodiments, the electrolyte solution includes hydroquinone, benzoquinone, and acetonitrile. Applying the voltage to the electrode may generate the hydroquinone at the cathode by reduction of the benzoquinone. The generated acid may travel from the anode to the cathode through the nanopore channel. Applying the voltage to the electrode may increase a rate of flow of the generated acid through the nanopore channel.

In one or more embodiments, the nucleotide includes a phosphoramidite monomer. Coupling the phosphoramidite monomer to the primer with the protecting group removed may include activating the phosphoramidite monomer with an azole. The azole may be selected from the group consisting of tetrazole, 2-ethylthiotetrazole, 2-benzylthiotetrazole, and 4,5-dicyanoimidazole.

In one or more embodiments, the method also includes stabilizing the intermediate product before step e. Stabilizing the intermediate product may include oxidizing a phosphite triester to a phosphate triester. The method may also include oxidizing the phosphite triester to the phosphate triester with a solution of iodine and pyridine.

In one or more embodiments, the method also includes capping an unreacted 5'-OH. Capping the unreacted 5'-OH may include reacting the unreacted 5'-OH with acetic anhydride and N-methylimidazole in tetrahydrofuran. Repeating steps b. to d. on the intermediate product may include coupling a different nucleotide to the intermediate product.

In one or more embodiments, the method also includes synthesizing a second oligonucleotide in a second nanopore channel of the nanofluidic device using steps a. to e. The second oligonucleotide may be different from the oligonucleotide. The method may also include a primary product interacting with the electrolyte solution to generate a secondary product. The plurality of electrodes and the plurality of nanopore channels may be contained in a fluidic or MEMS system. A size of the nanopore channel and an efficiency of producing the acid may increases an efficiency of the method of synthesizing the oligonucleotide.

In one or more embodiments, the method also includes synthesizing identical oligonucleotides in all nanopore channels of the plurality of nanopore channels. The voltage may be applied to all electrodes of the plurality of electrodes as a pulse with an amount of current. The voltage may be applied to all electrodes of the plurality of electrodes as a plurality of pulses with the amount of current. The voltage may be applied to the electrode in a stepwise manner. The method may also include varying the voltage applied to the electrode to vary the amount of acid produced from the electrolyte solution at the electrode.

In another embodiment, a method of synthesizing a plurality of different oligonucleotides using a nanofluidic array including a plurality of nanopore channels, a plurality of electrodes, and an electrolyte solution in the plurality of nanopore channel and in electrical contact with the plurality of electrodes, the method includes a. coupling first and second primers to respective inner walls of first and second nanopore channels of the plurality of nanopore channels, the first and second primers each having a protecting group. The method also includes b. applying a voltage to a first electrode of the plurality of electrodes that corresponds to the first nanopore channel to produce an acid from the electrolyte solution at the first electrode, where the first electrode includes a first anode and a first cathode disposed at opposite sides of the first nanopore channel, while not applying a voltage to a second electrode of the plurality of electrodes that corresponds to the second nanopore channel. The method further includes c the acid removing the protecting group from the first primer. Moreover, the method includes d coupling a first nucleotide to the first primer with the protecting group removed to form a first intermediate product. In addition, the method includes e repeating steps b. to d. on the first intermediate product and/or the second primer until the plurality of different oligonucleotides is synthesized.

In still another embodiment, a nanopore device for synthesizing an oligonucleotide includes a plurality of independently addressable electrodes defining a plurality of nanopore channels. The plurality of independently addressable electrodes form an array, such that each nanopore channel of the plurality of nanopore channels is independently addressable. The device also includes a pump to move fluid into and out of the plurality of nanopore channels. The device further includes a processor operatively coupled to the plurality of independently addressable electrodes, and the pump. The processor is programmed to instruct the plurality of independently addressable electrodes, and the pump to perform a method, the method includes a. pumping a primer into a nanopore channel of the plurality of nanopore channels, the primer having a protecting group, to couple the primer to an inner wall of nanopore channel. The method also includes b.

applying a voltage to an electrode of the plurality of independently addressable electrodes, to produce an acid from the electrolyte solution at the electrode. The method further includes c. the acid removing the protecting group from the primer. Moreover, the method includes d. pumping a nucleotide into the nanopore channel to couple the nucleotide to the primer with the protecting group removed to form an intermediate product. In addition, the method includes e. repeating steps b. to d. on the intermediate product until the oligonucleotide is synthesized.

In one or more embodiments, the electrode includes an anode and a cathode disposed at opposite sides of the nanopore channel. The anode and the cathode may be disposed at opposite ends of a longitudinal axis of the nanopore channel. The anode and the cathode may be disposed at opposite sides of the nanopore channel along a longitudinal axis of the nanopore channel. The plurality of independently addressable electrodes defining the plurality of nanopore channels may be contained in a fluidic or MEMS system. The nanopore device may be a 3D nanopore device. The processor may be programmed to instruct the plurality of independently addressable electrodes, and the pump to perform a method for synthesizing DNA, RNA, polypeptides, or aptamers. Each nanopore channel of the plurality of nanopore channels may be independently addressable by a respective electrode of the plurality of independently addressable electrodes.

In one embodiment, a method of synthesizing an oligonucleotide using a microfluidic device including a plurality of microchannels, a plurality of electrodes, and an electrolyte solution in the plurality of microchannel and in electrical contact with the plurality of electrodes, the method includes a. coupling a primer to an inner wall of a microchannel of the plurality of microchannels, the primer having a protecting group. The method also includes b. applying a voltage to an electrode of the plurality of electrodes that corresponds to the microchannel to produce an acid from the electrolyte solution at the electrode. The electrode includes an anode and a cathode disposed at opposite sides of the microchannel. The method further includes c. the acid removing the protecting group from the primer. Moreover, the method includes d. coupling a nucleotide to the primer with the protecting group removed to form an intermediate product. In addition, the method includes e. repeating steps b. to d. on the intermediate product until the oligonucleotide is synthesized.

In one embodiment, a method of synthesizing an oligonucleotide using a MEMS-based array device including a plurality of channels, a plurality of electrodes, and an electrolyte solution in the plurality of channel and in electrical contact with the plurality of electrodes, the method includes a. coupling a primer to an inner wall of a channel of the plurality of channels, the primer having a protecting group. The method also includes b. applying a voltage to an electrode of the plurality of electrodes that corresponds to the channel to produce an acid from the electrolyte solution at the electrode. The electrode includes an anode and a cathode disposed at opposite sides of the channel. The method further includes c. the acid removing the protecting group from the primer. Moreover, the method includes d. coupling a nucleotide to the primer with the protecting group removed to form an intermediate product. In addition, the method includes e. repeating steps b. to d. on the intermediate product until the oligonucleotide is synthesized.

Embodiments are not limited to nanopore arrays but also include larger pore sized array structures such as microarrays (pore size larger than 1000 nm) and MEMS-based arrays.

The aforementioned and other embodiments of the invention are described in the Detailed Description which follows.

BRIEF DESCRIPTION OF THE DRAWINGS

The drawings described below are for illustration purposes only. The drawings are not intended to limit the scope of the present disclosure. This patent or application file contains at least one drawing executed in color. Copies of this patent or patent application publication with color drawings will be provided by the U.S. Patent and Trademark Office upon request and payment of the necessary fee.

The foregoing and other aspects of embodiments are described in further detail with reference to the accompanying drawings, in which the same elements in different figures are referred to by common reference numerals, wherein.

Figure 1:
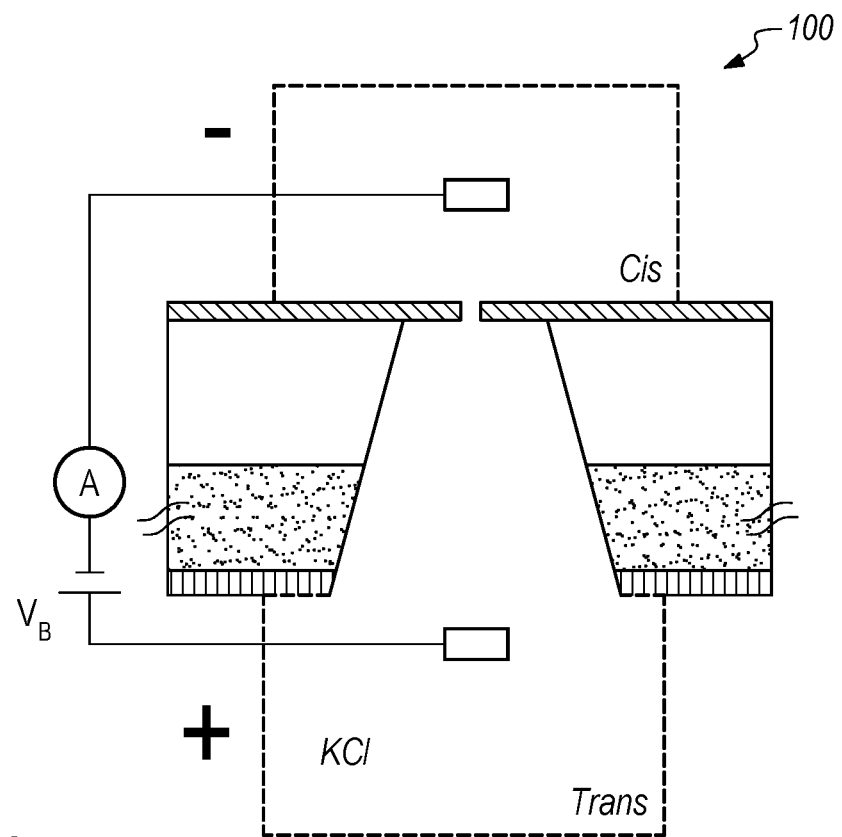
FIG. 1 schematically illustrates a prior art solid-state 2D nanopore device.

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

In order to address the above-described drawbacks (e.g., speed, flexibility cost, form factor, plug and play capability, scalability) of current biosynthesis technologies, multi-channel nanopore arrays that allow parallel synthesis of biomolecule may be used to achieve rapid synthesis of biomolecules with improved control and flexibility. Examples of multi-channel nanopore arrays (e.g., that may be used a sensors) are described in U.S. patent application Ser. Nos. 62/566,313, 62/593,840, 62/612,534, 62/628,214, 62/711,234, 16/147,362, 16/237,570, and 62/802,459, the contents of which have been previously incorporated by reference. Electrically addressing individual nanopore channels within multi-channel nanopore arrays can facilitate improved biosynthesis control and more efficient and effective use of multi-channel nanopore arrays to achieve low cost and high throughput synthesis of biomolecules.

Methods of efficiently and effectively synthesizing biomolecules using multi-channel nanopore arrays using individually electrically addressable nanopore channels with nanoelectrodes embedded in the nanopore arrays according to various embodiments are described below. Such biosynthesis with electrical addressing techniques can be used in solid-state nanopore arrays, biological arrays and hybrid nanopore arrays. Such biosynthesis with electrical addressing techniques can also be used with various multi-channel nanopore arrays, including the 3D multi-channel nanopore arrays described herein.

Exemplary Nanopore Devices

As described above, current state-of-art nanopore devices are limited at least in terms of sensitivity, electrical addressing, and manufacturing cost. The nanopore device embodiments described herein address, inter alia, these limitations of current nanopore devices.

Figure 2A:
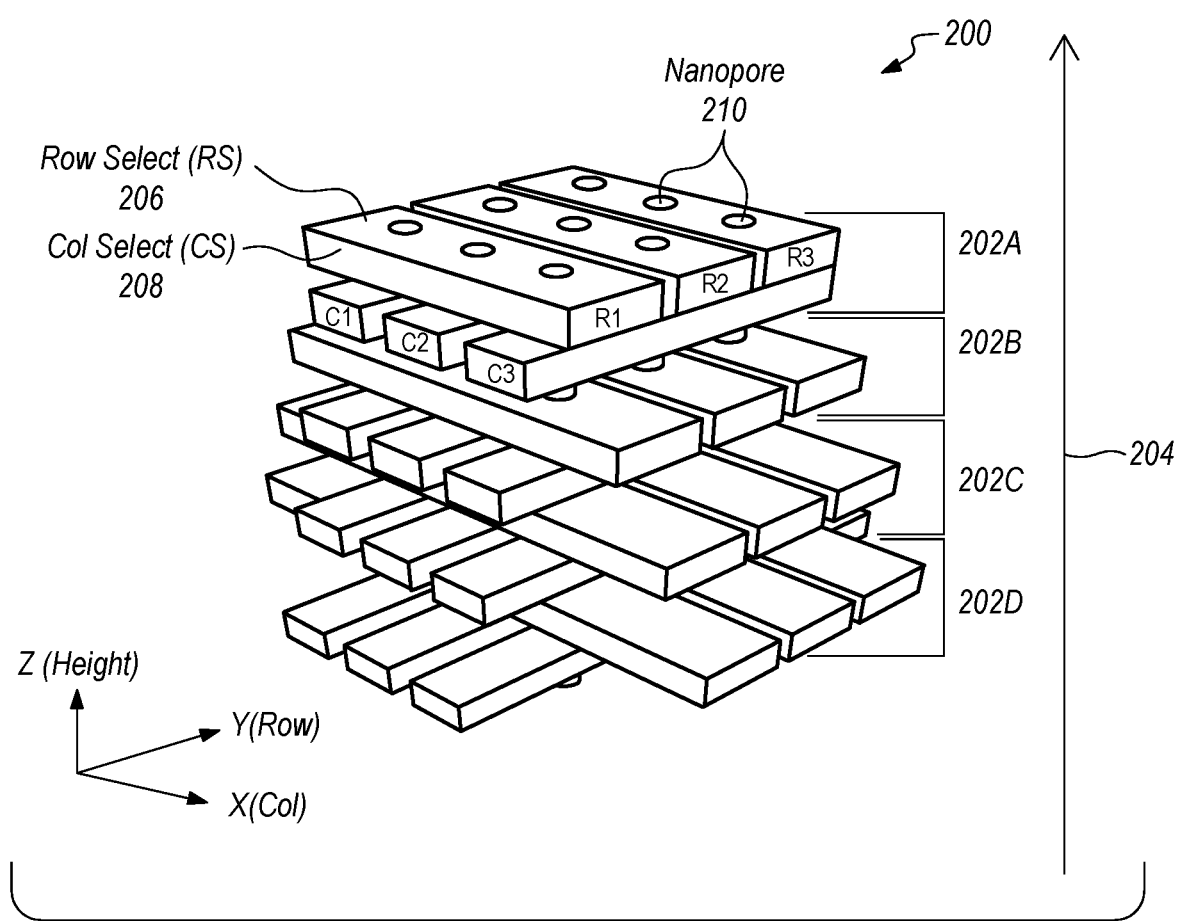
FIGS. 2A to 2D schematically illustrate a 3D schematic of a nanofluidic device with an embedded gate electrode system.
Figure 2B:
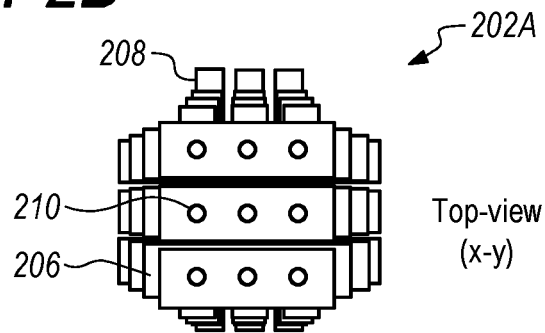
Figure 2C:
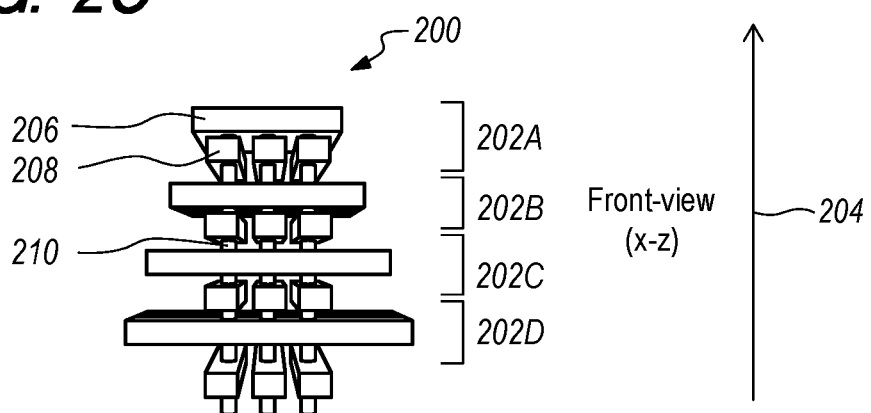
Figure 2D:
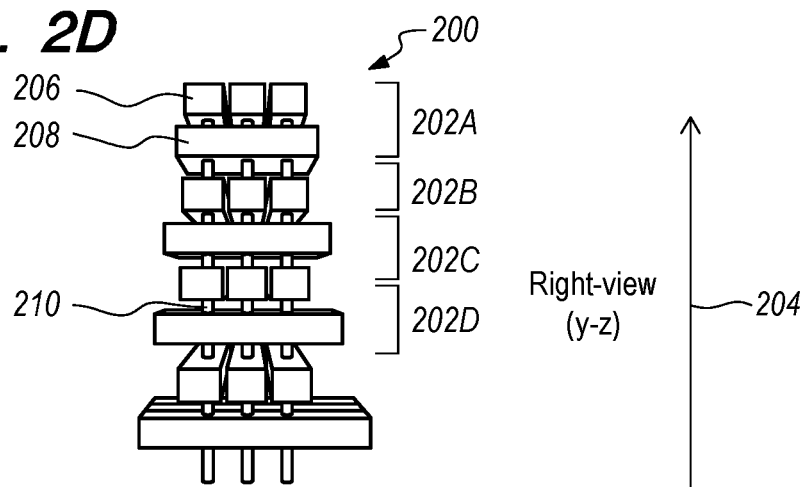

FIGS. 2A-2D schematically depict various views of a nanopore device 200 incorporating solid-state nanopore technology with a 3D array architecture according to one embodiment. As shown in FIG. 2A, the device 200 includes a plurality of 2D arrays or layers 202A-202D stacked along a Z axis 204. While the 2D arrays 202A-202D are referred to as "two dimensional," each of the 2D arrays 202A-202D has some thickness along the Z axis. FIG. 2B depicts a top view of the top 2D array 202A depicted in FIG. 2A. FIGS. 2C and 2D schematically depict front and right side views of the nanopore device 200 depicted in FIG. 2A.

The top 2D array 202A includes first and second selecting (electrode) layers 206, 208 configured to direct movement of charged particles (e.g., biopolymers) through the nanopores 210 (channels) formed in the first and second selecting layers 206, 208. The first selecting layer 206 is configured to select from a plurality of rows (R1-R3) in the 2D array 202A. The second selecting layer 208 is configured to select from a plurality of columns (C1-C3) in the 2D array 202A. In one embodiment, the first and second selecting layers 206, 208 select from the rows and columns, respectively, by modifying a charge adjacent the selected row and column and/or adjacent to the non-selected rows and columns. The other 2D arrays 202B-202D include nanoelectrodes that can be used for a variety of purposes (e.g., current/voltage application, rate control, current sensing, etc.) These nanoelectrodes may be made of highly conductive metals, such as Ta, Al, Au—Cr, TiN, TaN, Pt, Cr, Graphene, Al—Cu, polysilicon, etc. The nanoelectrodes may have a thickness of about 1~2 nm to about 1000 nm. The nanoelectrodes may also be made in the biological layer in hybrid nanopores.

In the embodiment shown in FIGS. 2A-2D, each of the arrays 202A-202D is a two dimensional array having first and second layers 206, 208 arranged in a cross pattern. In other embodiments (not shown), at least some of the arrays 202A-202D (e.g., 202B-202D) may be one dimensional arrays having only a single layer of that is selectively addressable along one axis. Two such single layer arrays may be selectively addressable along respective axes that are orthogonal to each other. While the embodiment shown in FIGS. 2A-2D has four arrays 202A-202D, other embodiments (not shown) may have fewer or more layers.

Hybrid nanopores include a stable biological/biochemical component with solid-state components to form a semi-synthetic membrane porin to enhance stability of the nanopore. For instance, the biological component may be an αHL molecule. The αHL molecule may be inserted into a SiN based 3D nanopore. The αHL molecule may be induced to take on a structure to ensure alignment of the αHL molecule with the SiN based 3D nanopore by apply a bias to an electrode (e.g., in the top 2D array 202A).

The nanopore device 200 has a 3D vertical channel stack array structure that provides a much larger surface area for voltage application and biosynthesis reactions than that of a microarray biosynthesis device and even that of a conventional nanopore device having a planar structure. As various charged particles (e.g., bioactive molecules) pass through each 2D array 202A-202D in the device, the charged particles can react with other molecules (e.g., other bioactive molecules) linked to an inner surface of the nanopore channels in the nanopore device 200. Electrically addressing individual nanopore channels in the nanopore device 200 facilitates application of voltages to individual nanopore channels, which provide precise control of electrochemical reactions at individual nanopore channels. Therefore, the 3D array structure of the device 200 and individual electrical addressing facilitates increased surface area for biosynthesis reactions and more precise control of electrochemical reactions. Further, the highly integrated small form factor 3D structure provides a high density nanopore array while minimizing manufacturing cost and form factor.

In use, the nanopore device 200 is disposed in a middle chamber (not shown) between and separating top and bottom chambers (not shown) such that the top and bottom chambers are fluidly coupled by the middle chamber and the nanopore channels 210. The top and bottom chambers include an electrode (e.g., metal, polymer, polysilicon, etc.) and electrolyte solutions (e.g., hydroquinone and benzoquinone in acetonitrile) containing the bioactive molecules (e.g., a nucleoside phosphoramidite monomer) to be used in synthesizing biomolecules. Different electrode and electrolyte solutions can be used for the synthesis of different biomolecules.

Electrophoretic charged particle (e.g., H+) translocation can be driven by applying a voltage/potential/bias to electrodes disposed in a top chamber (not shown) adjacent the top 2D array 202A of the nanopore device 200 and a bottom chamber (not shown) adjacent the bottom 2D array 202D of the nanopore device 200. In some embodiments, the nanopore device 200 is disposed in a middle chamber (not shown) between top and bottom chambers (not shown) such that the top and bottom chambers are fluidly and therefore electrically coupled by the nanopore channels 210 in the nanopore device 200 in the middle chamber. The top and bottom chambers may contain the electrolyte solution to electrically couple anodes and cathodes in the top and bottom chambers.

Exemplary Nanopore Device Electrical Addressing Scheme

FIGS. 2A-2D depict, in perspective, top, and cross-sectional views, the nanopores 210 and the electrode (e.g., nanoelectrode) schemes according to one embodiment. In this embodiment, the nanopore 210 is surrounded by nanoelectrodes, allowing the nanopore 210 channel to be controlled under nanoelectrode electrical bias field conditions.

The first and second selecting layers 206, 208 include cross-patterned nanogap electrodes that function as column and row electrodes for the nanopore array device 200, respectively. These electrodes can be used to independently address nanopore 210 channels of the nanopore array device 200. Cross-patterned nanogap electrodes in the first and second selecting layers 206, 208 (see x-y plane view in FIG. 2B) are patterned using metal lithography techniques and the remaining electrodes in the other layers (202B-202D) are also deposited with cross-patterned or deposited with plane metal or poly gate electrodes. All the nanopore 210 channels are completely surrounded by the metal or polysilicon electrodes and thus under the full influence of the electrical bias applied on the multiple stacked electrodes (in layers 202A-202D). By applying voltages/potentials/biases to various nanogap electrodes in layers 202A-202D, voltages/potentials/biases can be applied across various nanopore 210 channels. For instance, applying voltages/potentials/biases across layer 202A and layer 202D at selected particular nanopore 210 channels can selectively drive electrochemical reactions at those nanopore 210 channels and ionic translocation of charged particles (e.g., H+) through the selected nanopore 210 channels (e.g., from a top chamber to a bottom chamber orthogonal to the planes of the electrodes).

Exemplary Nanopore Biosynthesis Devices and Methods

Exemplary Nanopore Biosynthesis Devices

The nanopore biosynthesis devices and methods described herein involve 3D nanofluidic arrays. In some embodiments, the nanopore biosynthesis devices and methods utilize a phosphoramidite oligonucleotide strategy and various nanoelectrode configurations and electrical control schemes to control various electrochemical reactions and charged particle translocation for biomolecule synthesis. Using nanochannel arrays reduces the system size and corresponding sample and reagent size and system footprint. Further, using nanoelectrodes to independently and selectively address nanochannels provides improved control of the biosynthetic reactions.

Figure 3:
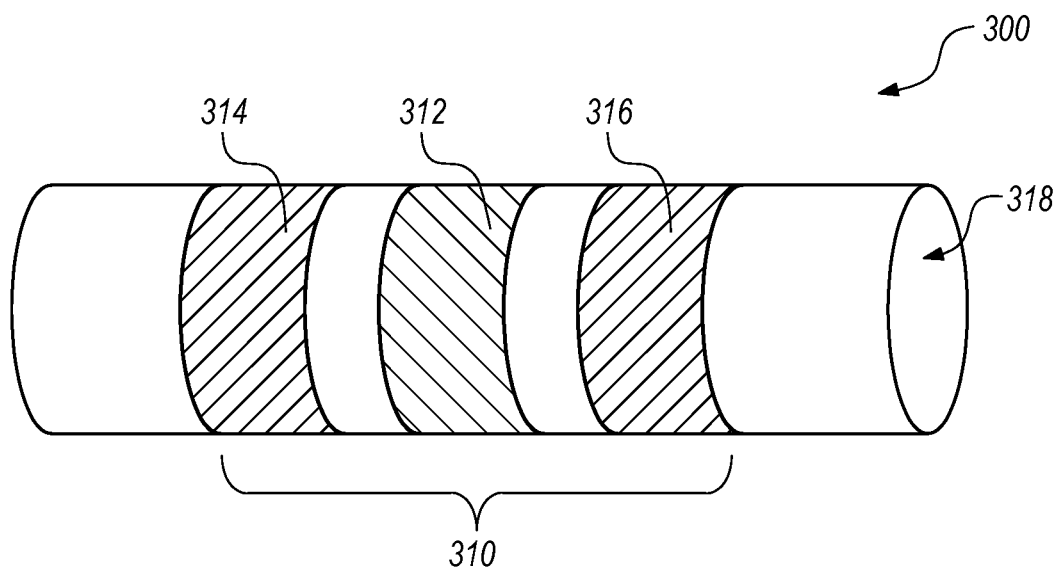
FIG. 3 schematically illustrates even and odd electrodes (cathodes and anode) for biomolecular synthesis systems and methods according to some embodiments.
Figure 4:
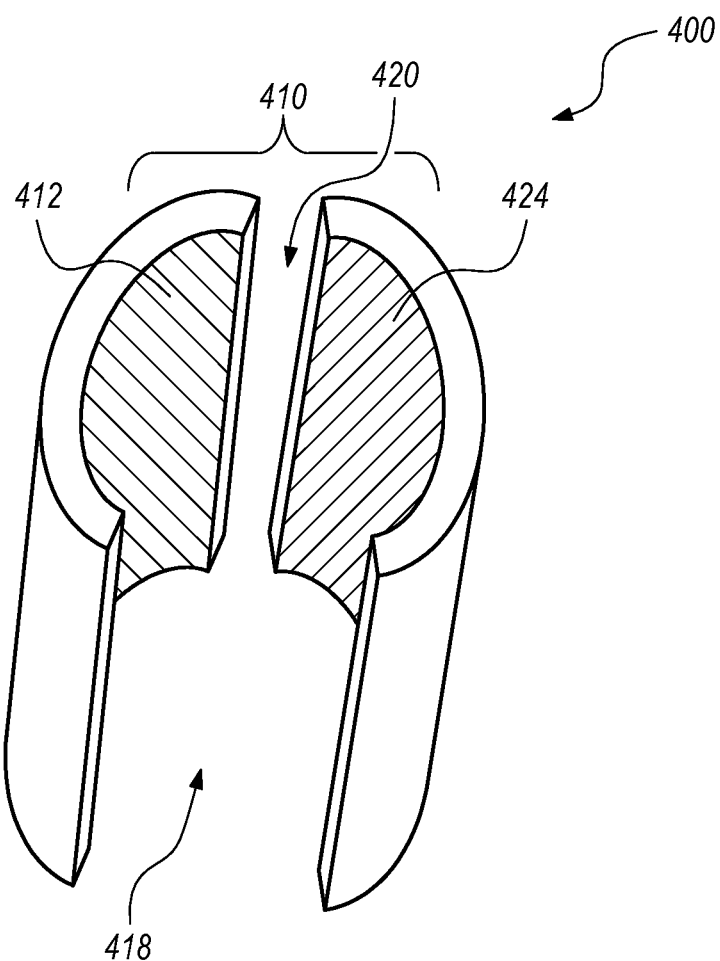
FIG. 4 schematically illustrates segmented electrodes (cathode and anode) for biomolecular synthesis systems and methods according to some embodiments.

FIGS. 3 and 4 depict nanoelectrode configurations according to various embodiments. FIG. 3 depicts a nanoelectrode 310 having an anode (+) 312 disposed between a pair of cathodes (−) 314, 316, according to one embodiment. The nanoelectrode 310 defines portions of a nanochannel 518. Charged particles (e.g., H+) formed at the anode 312 (e.g., electrochemically) are driven by ionic translocation through the nanochannel 318 to the cathodes 314, 316. In this operation, electrical bias between the two electrodes can range from 0.1 volt to 10V depending on the inter-electrode and gate dielectric thickness which can range between 5 nm and 100 nm.

FIG. 4 depicts a nanoelectrode 410 having an anode (+) 412 and a cathode (−) 414 that form two portions of a cylinder split along a longitudinal plane that a separated by a space 420. The anode 412 and the cathode 414 form a portion of a nanochannel 418. Charged particles (e.g., H+) formed at the anode 412 (e.g., electrochemically) are driven by ionic translocation across the nanochannel 418 to the cathode 414. In this mode of operation, electrical bias between the two electrodes can range from 0.1 volt to 10V depending on the size of the electrode gap and dielectric thickness which has a range between 5 nm to 100 nm.

The polarity of the nanoelectrodes 310, 410 described above can be switched such that the anode becomes a cathode and the cathode(s) become anode(s), The nanoelectrodes 310, 410 are complete rings 310 and interrupted rings 410 that define portions of the nanochannel/nanopore 418, thereby allowing the field to be applied in three dimensions along the nanochannel/nanopore 418.

Switching the polarity of the nanoelectrodes 310, 410 can facilitate the formation of charged particles in various regions of the nanoelectrodes 310, 410 and improved movements and distribution of the charged particles throughout the nanochannels 318, 418, thereby increasing the biomolecule synthesis throughput.

Figure 5:
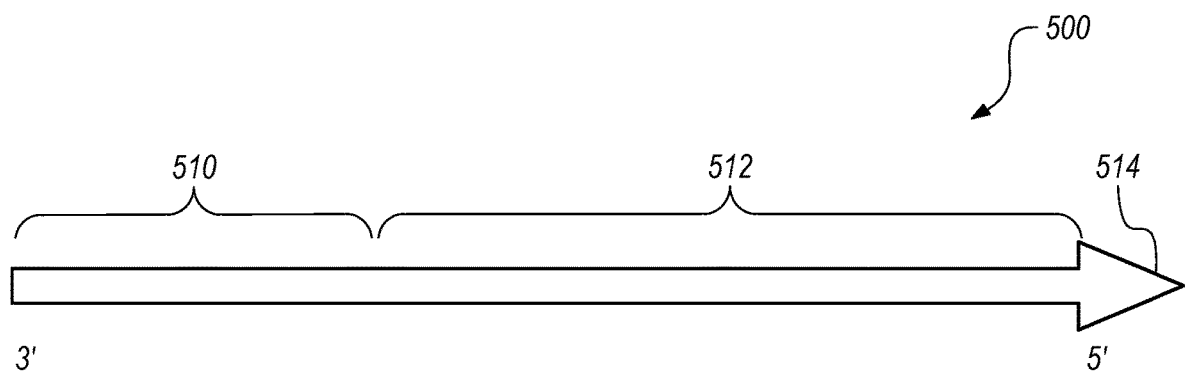
FIG. 5 schematically illustrates a primer for use with biomolecular synthesis systems and methods according to some embodiments.

Biomolecule synthesis can be initiated from a primer coupled to an inner wall of a nanopore channel. In some embodiments, an oligonucleotide primer 500 may include a binding portion 510 at a 3' end and a "barcode chain" 512 with a protecting group 514 at its 5' end to protect/block the 5' end from biochemical reactions, as shown in FIG. 5. The binding portion 510 is configured to couple to a surface of a nanopore channel. The "barcode chain" may be a small oligonucleotide fragment.

Nanopore array biosynthesis systems according to some embodiments include a nanofluidic system including a pump and a fluid dispenser that are both computer-controlled. The nanofluidic system can include a fluid inlet and a fluid outlet located at opposite ends of the nanopore array biosynthesis system such that as a fluid is pumped from the inlet to the outlet, the entire nanopore array biosynthesis system is exposed to the fluid and the reactants contained therein. Various fluids that can be pumped through the nanofluidic system and the nanopore array biosynthesis system include initial electrolyte solution (hydroquinone and benzoquinone with tetrabutylammonium hexafluorophosphate in anhydrous acetonitrile), nucleoside phosphoramidite monomer solution (with ETT activator solution), oxidizing solution (THF/Water/Pyridine/Iodine), THF/Acetic anhydride and THF/Pyridine/N-methylimidazole for capping process after adding each nucleotide to prevent unwanted bonding, which may cause mutation in the synthetic chain, and washing/dissolving solution (acetonitrile). These solutions are pumped into the nanofluidic system and the nanopore array biosynthesis system during various reagent fill and wash steps corresponding to reaction steps and stages in a phosphoramidite oligonucleotide synthesis reaction. The processor controlling the pump and fluid dispenser is programmed to permit adequate time between reagent fill and wash steps to allow completion of reaction steps.

The inner surfaces of the nanochannels of the nanopore array biosynthesis system can be dressed/coated/covered with a polymer as a masking element. The binding portion of the primer can be linked to this dress polymer. After synthesis of the oligonucleotide is completed, the dress polymer can be dissolved and removed from the nanochannels to render the nanopore array reusable. Exemplary dress polymers include, but are not limited to, polyethylene glycol (PEG 5000) monomethyl ester, poly esters, aliphatic polyester, temperature resistant polymers, aliphatic homopolymers, polycaprolactons, polymers with cosolvents, polar polymers, hydrophilic polymers, and hydrophobic polymers. This dress polymer can be heat resistance and can be detached by raising the temperature. Alternatively, the dress polymer can be labile and removable by raising the pH of in the nanochannels. Alternatively, the dress polymer can be a photo resist and removable by treatment with UV light. The dress polymer can be any type of masking polymer for protecting the inner surface of the nanochannel that can be removed using corresponding treatments for detaching or de-masking.

During transport and before use the nanopore channels are electrically isolated from the anode to minimize degradation. An inner surface of the nanopore channels acts as a solid-state substrate for biosynthesis. For oligonucleotide synthesis, substantial portions of the inner surface of the nanopore channels are formed from electrodes (see FIGS. 3 and 4), which can be made of metal, polymer, or polysilicon electrodes and derivatized with (3-glycidoxypropyl)-trimethoxysilane and a polyethylene glycol linker.

An underlying dimethoxytrityl (DMT) layer facilitating dA buildup is then added over the inner surface of the nanopore channel, which give the inner surface of the nanopore channel a DMT gathering property during a first deblocking step, described below. Alternatively, acetic acid in dichloromethane can be utilized instead of the above-described hydroquinone and benzoquinone with tetrabutylammonium hexafluorophosphate in anhydrous acetonitrile electrolyte.

Figure 6:
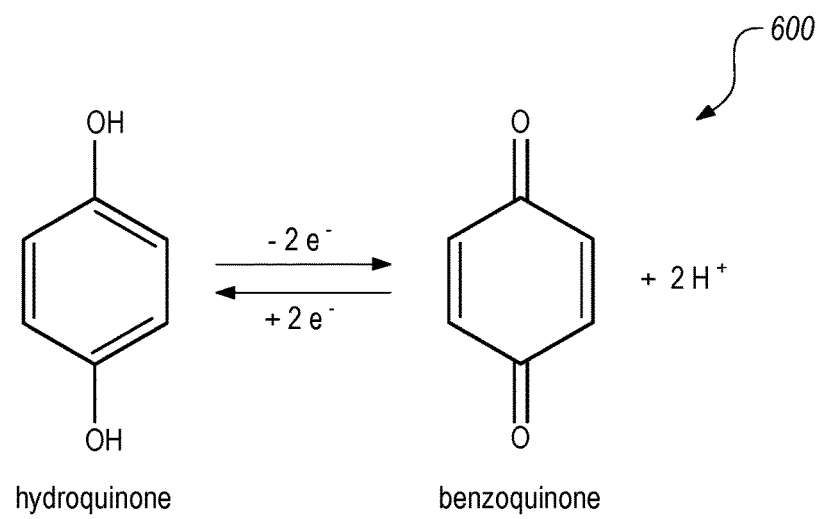
FIG. 6 schematically illustrates the transition between hydroxyquinone and benzoquinone according to some embodiments.

The catalyst for phosphoramidite oligonucleotide synthesis is acid (H+), which can be provided electrochemically in the nanopore array biosynthesis system. The H+ ions can be generated by oxidation of hydroxyquinone to benzoquinone as shown in the chemical equation 600 in FIG. 6. The H+ ions also deblock/deprotect the 5' end of the growing oligonucleotide as described below.

Exemplary Nanopore Biosynthesis Methods

Figure 7:
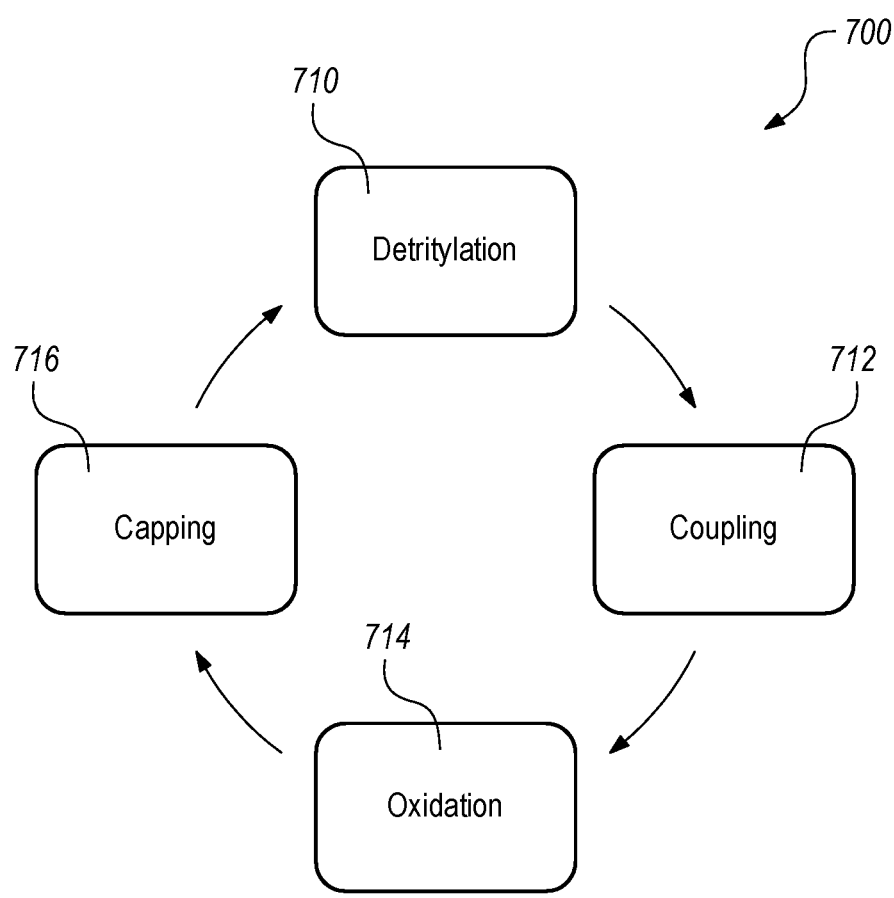
FIGS. 7 and 8 schematically illustrate solid phase phosphoramidite oligonucleotide synthesis according to some embodiments.
Figure 8:
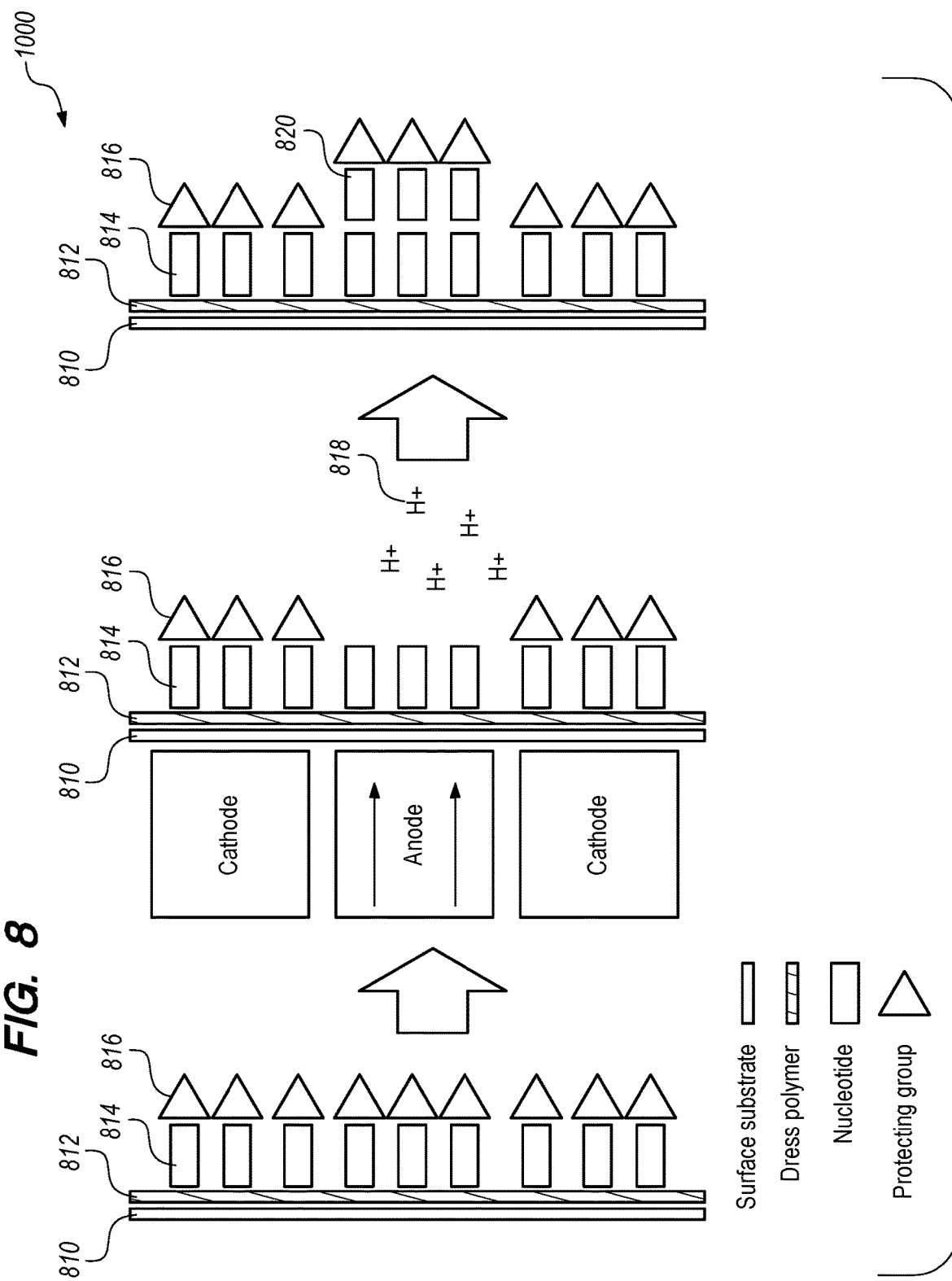

FIGS. 7 and 8 depict a method 700 of solid phase phosphoramidite oligonucleotide synthesis according to some embodiments. The method 700 begins with a oligonucleotide primer 814 coupled/linked to a dress polymer 812 on the inner surface 810 of a nanopore channel as described above and as shown in FIG. 9. The oligonucleotide primer 814 is protected/blocked with a protecting group 816.

At 710, the protecting group 816, which in some embodiments is DMT is removed from the 5' of the primer 1014 by H+ 818 as shown in FIG. 8. The H+ is generated by oxidation of hydroxyquinone to benzoquinone from the initial electrolyte solution described above (e.g., hydroquinone and benzoquinone with tetrabutylammonium hexafluorophosphate in anhydrous acetonitrile) driven by a voltage/potential/bias applied across the electrode (e.g. anode/cathode) corresponding to the nanopore channel as described above. Removal of the DMT protecting group 816 is called detritylation. Detritylation results in a highly reactive free 5'-OH group at the 5' of the primer 1014 adjacent the anode as shown in FIG. 8.

At 712, nucleoside phosphoramidite monomer solution (with ETT Activator solution, 0.25M) is pumped into the nanopore array biosynthesis system displacing the initial electrolyte. In some embodiments, the system may be washed before adding the nucleoside phosphoramidite monomer solution. The processor instructs the pump to add the nucleoside phosphoramidite monomer 820 corresponding to the next nucleotide in the target oligonucleotide. The nucleoside phosphoramidite monomer 820 is activated by the catalyst. The catalysts can be an azole, such as tetrazole, 2-ethylthiotetrazole, 2-benzylthiotetrazole, and 4,5-dicyanoimidazole. The catalyzed/activated nucleoside phosphoramidite monomer 820 reacts with the detritylated 5' end of the deprotected primer 814, and is added to the growing oligonucleotide as a phosphoramidite monomer 820. During the coupling reaction, a nucleoside reacts with the phosphorus of the approaching catalyzed/activated nucleoside phosphoramidite monomer, uprooting its diisopropylamino group.

At 714, oxidizing solution (iodine in pyridine, water, and tetrahydrofuran) is pumped into the nanopore array biosynthesis system displacing the nucleoside phosphoramidite monomer solution. In some embodiments, the system may be washed before adding the oxidizing solution. Oxidation changes the unstable phosphite triester formed during the coupling reaction to a stable phosphate triester, which allows the method to return to step 910 (detritylation of the second nucleoside) for the next cycle to add another nucleoside to the oligonucleotide.

At 716, before moving back to step 710 in the cycle, unreacted nucleosides attached to the nanopore channel wall are "capped." A capping solution (acetic anhydride and N-methylimidazole in tetrahydrofuran) is pumped into the nanopore array biosynthesis system displacing the oxidizing solution. In some embodiments, the system may be washed before adding the capping solution. The capping solution acetylates the 5'-OH on the unreacted nucleosides attached to the nanopore channel wall. This prevents further reaction of the unreacted nucleosides, which would otherwise form unintended oligonucleotides with various deletions. Capping the unreacted nucleosides also increases the efficiency of subsequent cycles in the biosynthesis method. After capping, the method may move back to step 710 (detritylation of the last added nucleoside) to add another nucleoside to the growing oligonucleotide until the oligonucleotide is complete.

The nanopore array biosynthesis systems and methods described herein involve oligonucleotide synthesis inside nanopore channels that are independently the via nanoelectrodes including anodes and cathodes (see FIGS. 3 and 4) at forum portions of the nanochannel. The anodes electrochemically generate protons (H+) that move to the cathodes the ionic translocation. These generated protons (H+) sever the corrosive labile dimethoxytrityl group to allow coupling of nucleoside phosphoramidite monomers. The protons (H+) can also deprotect/deblock various other protective groups according to various embodiments.

The number of cycles in the solid phase phosphoramidite oligonucleotide synthesis method 700 depends on the desired length of the target oligonucleotide. The upper limit of current solid phase phosphoramidite oligonucleotide synthesis methods, due to oligonucleotide union, is around 200 rounds, which would result in oligonucleotides of around 200 nucleotides in length. More typical solid phase phosphoramidite oligonucleotide synthesis methods involve 5-100 cycles. Solid phase phosphoramidite oligonucleotide synthesis methods according to some embodiments involve 10-25 cycles.

Similar devices and methods can be used for solid phase polypeptide synthesis. Due to polypeptide amalgamation, the upper limit of current solid phase polypeptide synthesis methods is around 75-100 cycles, which would result in polypeptides of around 75-100 amino acids in length. More typical solid phase polypeptide synthesis methods involve 5-50 cycles. Solid phase polypeptide synthesis methods according to some embodiments involve 5-25 cycles, which would result in polypeptides of 5-25 amino acids in length.

In order to determine product quality of solid phase phosphoramidite oligonucleotide synthesis products, the unrefined oligonucleotide can be characterized using HPLC, PAGE, or gel capillary electrophoresis ("CE"), according to various embodiments. Determining the amount of DMT using HPLC, PAGE, or can determine product quality while limiting the time required for analysis, purification and/or fluorescent staining. In some embodiments, the 3D nanopore array can also be used as a sensor to measure the charge for each nanopore channel.

Electrochemical Mechanisms

The plurality of independently addressable nanoelectrodes allows a processor to independently control the voltages applied to each of the plurality of nanopore channels in the 3D nanopore array biosynthesis systems. Different voltages can be applied (or not applied in case of zero voltage) to each of the nanopore channels that are independently addressed by corresponding nanoelectrodes.

In some embodiments, all of the nanopore channels can be utilized to synthesize the same oligonucleotide by applying the same voltage to all of the nanopore channels. In other embodiments, different nanopore channels can be utilized to synthesize different oligonucleotides by applying different voltages to the different nanopore channels. Further, some nanopore channels can be in activated during biosynthesis by not applying any voltage to those nanopore channels. This flexibility of control over biosynthesis at the nanopore channel level allows efficient synthesis of an oligonucleotide and/or a mixture of different oligonucleotides in a minimal amount of time.

Protons (H+) generated at one nanopore channel have minimal effect on biosynthesis at other adjacent nanopore channels because the proton (H+) diffusion profile is anisotropic, with most of the generated protons (H+) diffusing into the nanopore channel instead of along the outer surfaces of the 3D nanopore array. This anisotropic diffusion can be driven by ionic translocation resulting from the voltage applied across the electrodes. As such, the protons (H+) generated at one nanopore channel are concentrated at that nanopore channel and substantially isolated from other nanopore channels.

Portions of the outer surfaces of the 3D nanopore array between nanopore channels can be deprotected and synthetically rendered chemically inert before formation of the nanopore channels in order to generate barriers to prevent unintended detritylation. These barriers increase the distance that generated protons (H+) must diffuse before reacting with an available protecting group (e.g., DMT). These barriers further isolate the biosynthetic reactions in the nanopore channels from each other.

Figure 9:
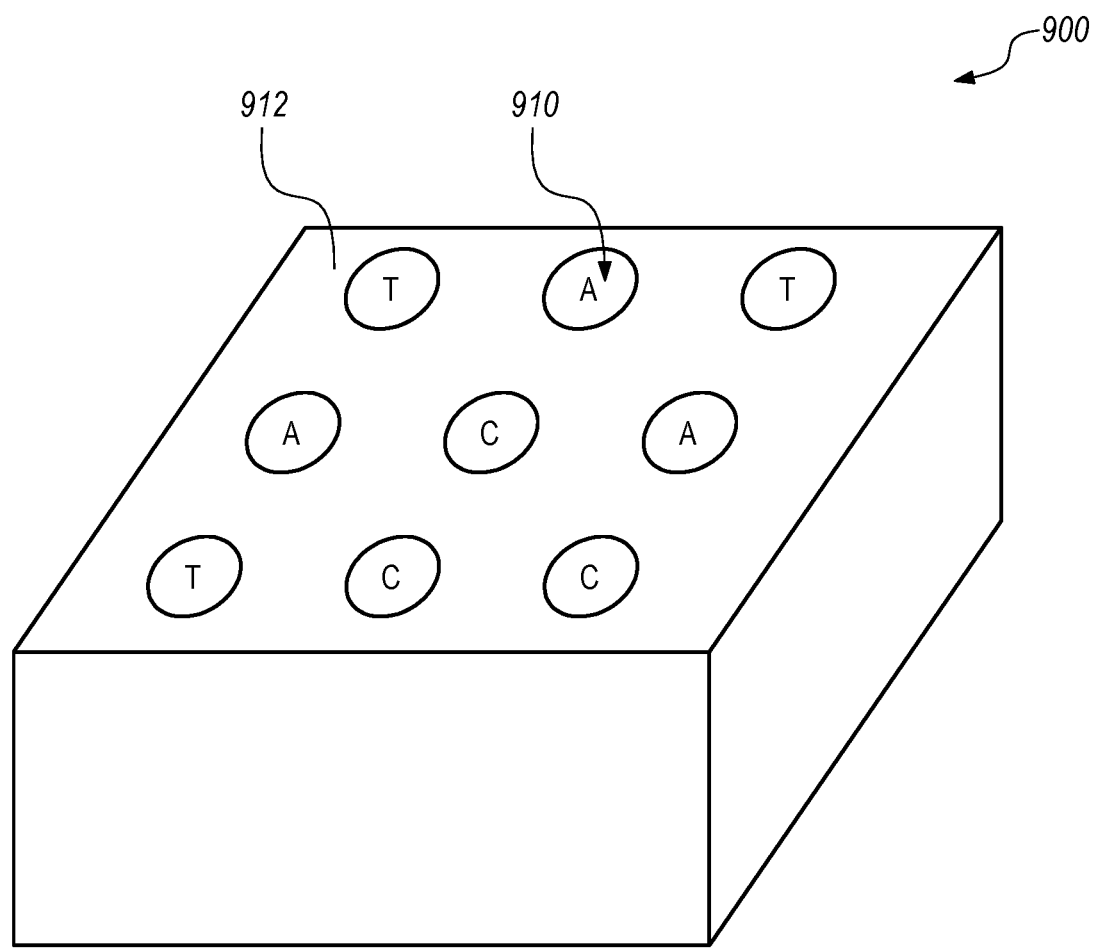
FIG. 9 schematically illustrates a 3D nanopore array biosynthesis system according to some embodiments.

For instance, FIG. 9 depicts a 3D nanopore array biosynthesis system 900 according to some embodiments. The system 900 includes a plurality of nanopore channels 910 that are separated by the outer surface 912 of the system 1100. As shown in FIG. 9, the system is simultaneously generating a plurality of different oligonucleotides. For instance the last nucleotide added to various ones of the plurality of different oligonucleotides include adenine A, thymine T, and cytosine C.

Figure 10:
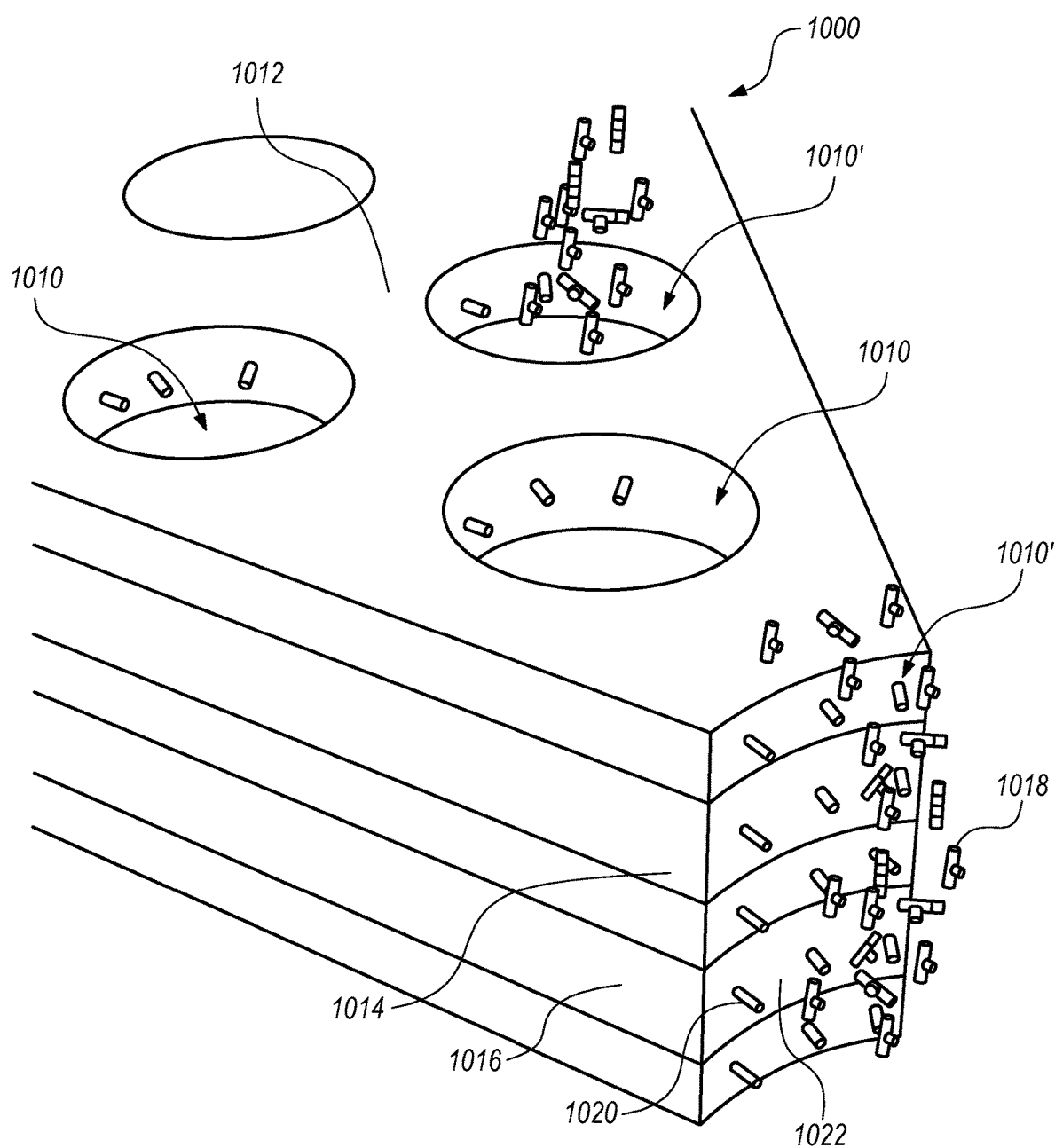
FIG. 10 schematically illustrates a 3D nanopore array biosynthesis system according to some embodiments.

FIG. 10 schematically illustrates a 3D nanopore array biosynthesis system 1000 according to some embodiments. The 3D nanopore array biosynthesis system 1000 defines a plurality of nanopores/nanochannels 1010, 1010' that are separated by the outer surface 1012 of the system 1000. The nanopores/nanochannels 1010, 1010' extend through the 3D nanopore array 1000. The 3-D nanopore array biosynthesis system 1000 also includes an anode 1014 and a cathode 1016.

As shown in FIG. 10, some of the nanopores/nanochannels 1010' are selected by applying an electrical potential to nanoelectrodes that address the selected nanopores/nanochannels 1010'. Other nanopores/nanochannels 1010 are not selected because no electrical potential has been applied to the nanoelectrodes that address those nanopores/nanochannels 1010. Nucleoside phosphoramidite monomers 1018 into the selected nanopores/nanochannels 1010' where they interact with the oligonucleotide primers 1020 coupled to an interior surface 1022 of the selected nanopores/nanochannels 1010', as shown in FIG. 8 above.

Figure 11:
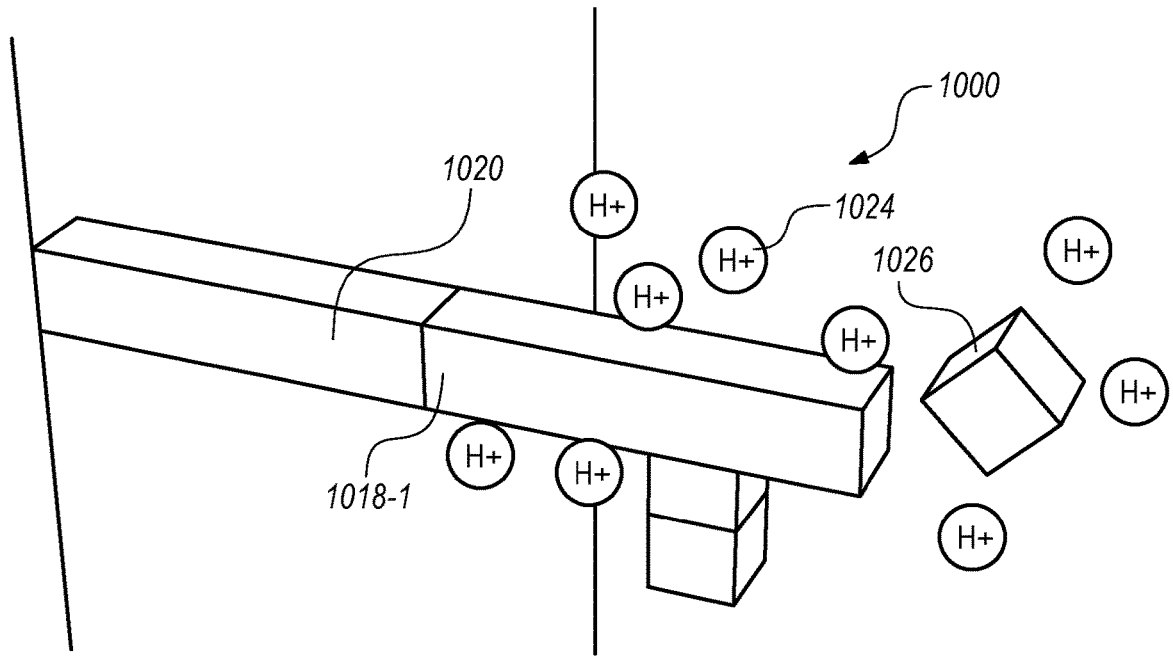
FIG. 11 schematically illustrates detritylation in 3D nanopore array biosynthesis systems and methods according to some embodiments.

FIG. 11 schematically illustrates detritylation in a 3D nanopore array biosynthesis system 1000 and methods according to some embodiments. By applying an electrical field in a 3D nanopore array biosynthesis system 1000 (see FIG. 10), hydrogen atoms 1024 are released/generated in the electrolyte solution in the nanopore/nanochannel. The hydrogen atoms 1024 remove the cap (e.g., DMT) 1026 from the nucleoside phosphoramidite monomer 1018 at the growing end of biomolecule/biopolymer being synthesized in the system 1000, as depicted in FIGS. 7 and 8, and described above. The nucleoside phosphoramidite monomer 1018-1 in FIG. 11 is the first monomer in the growing biomolecule/biopolymer attached to the oligonucleotide primer 1020.

Figure 12:
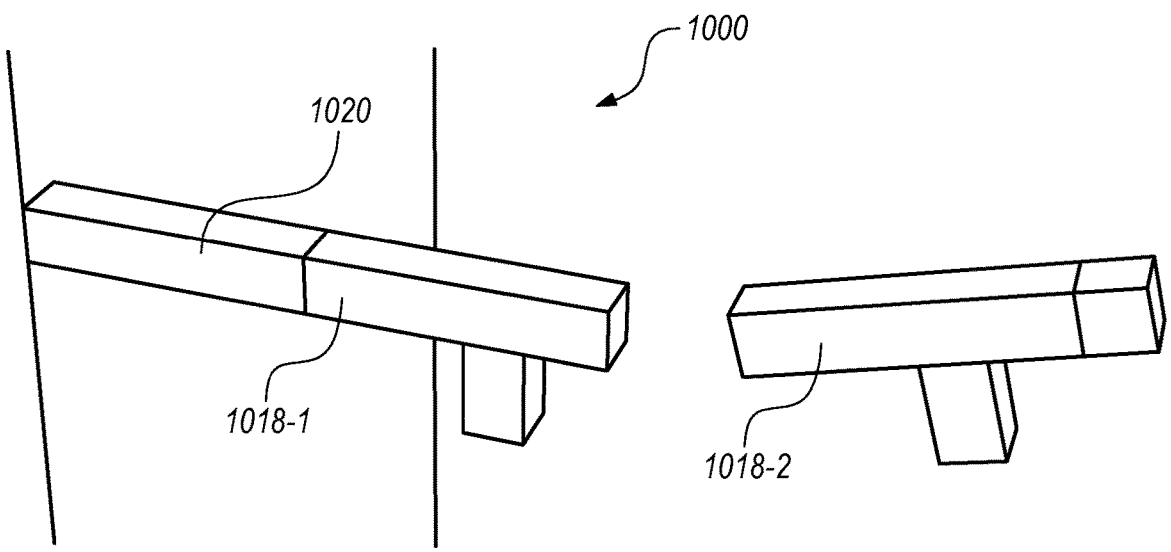
FIGS. 12-14 schematically illustrates various steps in a 3D nanopore array biosynthesis method according to some embodiments.
Figure 13:
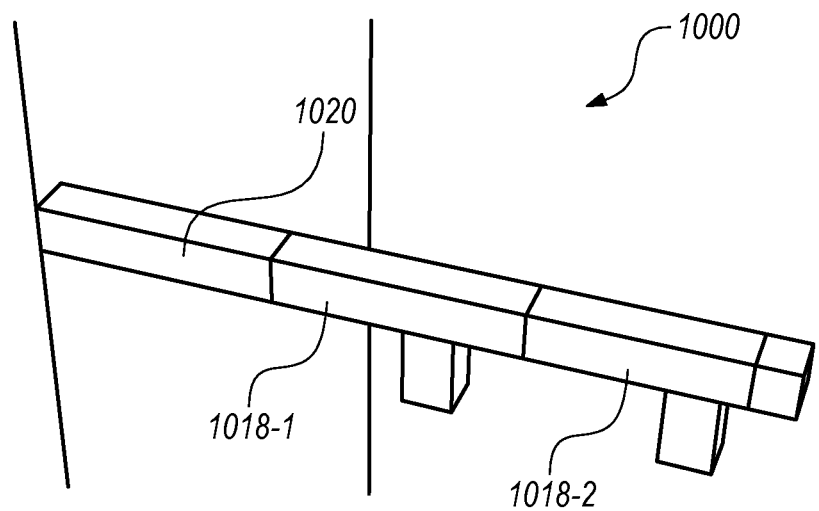
Figure 14:
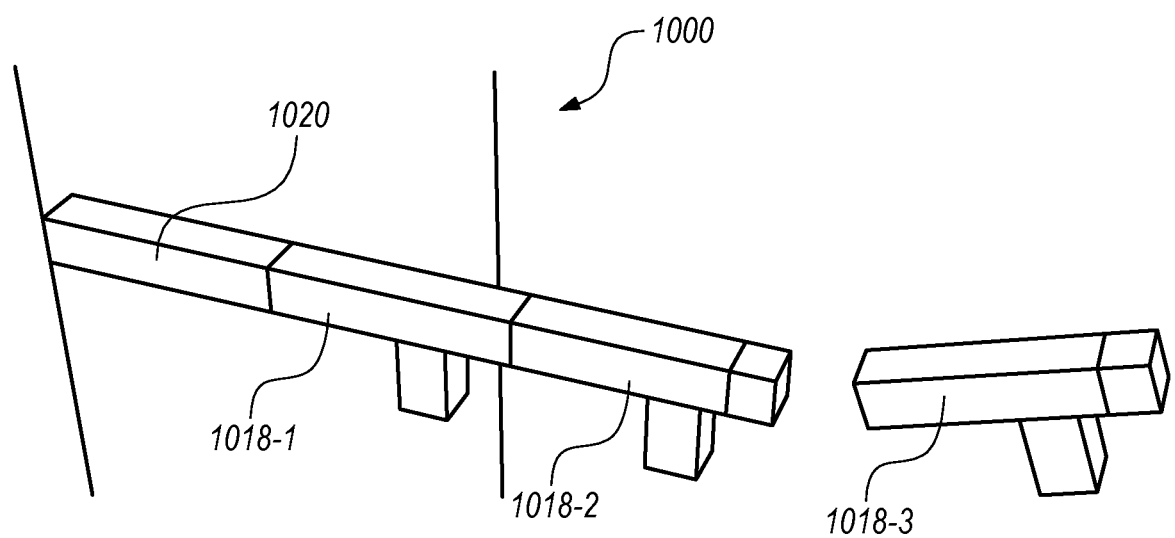

FIGS. 12-14 schematically illustrates various steps in a 3D nanopore array biosynthesis method according to some embodiments. In FIG. 12, which follows FIG. 11, a second nucleoside phosphoramidite monomer 1018-2 approaches the uncapped first nucleoside phosphoramidite monomer 1018-1. In FIG. 13, which follows FIG. 12, the second nucleoside phosphoramidite monomer 1018-2 has been coupled to the first nucleoside phosphoramidite monomer 1018-1, as depicted in FIGS. 7 and 8, and described above. By repeating the uncapping and coupling steps shown in FIG. 7, a third nucleoside phosphoramidite monomer 1018-3 can be added to the growing biomolecule/biopolymer (see FIG. 14, which follows. FIG. 13). By repeating the uncapping and coupling steps, and by controlling the nucleoside phosphoramidite monomer 1018 present in the selected nanopore/nanochannel during. Each coupling step, this method can accurately and rapidly synthesize biomolecules/biopolymers.

During manufacturing of 3D nanopore arrays (including nanopore channels), proton foragers can be used to minimize the unintended presence of protons (H+) in areas of the 3D nanopore array. Proton foragers can be electrochemically produced by disposing a ground terminal in the middle of the substrate of 3D nanopore array to act as a sink to forage protons (H+). In other embodiments, other weaker proton foragers can be utilized during manufacturing of the 3D nanopore arrays. Minimizing the unintended presence of protons (H+) increases the efficiency of the solid phase phosphoramidite oligonucleotide synthesis reactions.

An ASIC for use with this 3D nanopore array biosynthesis system can be programmed to instruct an operatively coupled power supply to deliver voltages/potential/biases to specific nanoelectrodes to independently address specific nanopore channels in order to control biosynthetic reactions in the specific nanopore channels. The 3D nanopore array biosynthesis system can be disposed in a microfluidic chamber (e.g., having top, middle, bottom chambers). The ASIC is also operatively coupled to one or more pumps to provide instructions for filling the microfluidic chamber with various reaction solutions (see above), and for flushing the microfluidic chamber before adding a new reaction solution. As described above, 3D nanopore array biosynthesis system can synthesize safe variety of biomolecules (e.g., oligonucleotides, oligopeptides, etc.) using the generation of protons (H+) at the anode to deprotect the growing end of various biopolymers. The ASIC/processor can be programmed to control all voltages, timing, anode/cathode assignments, and to sense/detect an estimated current in various nanoelectrodes.

In the 3D nanopore array biosynthesis systems, the synthesis mechanism is addressable at the nanopore channel level. Each nanopore channel is an independent reaction chamber with an electrode operatively coupled thereto. By independently applying positive and negative voltages/potential/biases to a nanopore channel, the synthesis mechanism in that nanopore channel can be independently initiated to synthesize the biomolecule of interest by removing the acid labile protecting group and performing the synthesis.

The 3D nanopore array biosynthesis systems and methods can be used to generate a wide variety of biomolecules including oligonucleotides that can be used to detect and address numerous diverse genomic issues at various stages. Simple and rapid diagnostic strategies are facilitated by the oligonucleotides generated using the 3D nanopore array biosynthesis systems and methods described herein (e.g., oligonucleotide probes corresponding to various cancers).

The 3D nanopore array biosynthesis systems and methods including independently addressable nanoelectrodes and nanopore channels described herein enhance the surface to volume ratio of biosynthesis systems and minimize the form factor for clinical, scientific, and industrial applications as well as portable applications. In addition, a small form factor can facilitate Lab-on-a-Chip applications, which can function as a center inside clinical and MEMS frameworks.

Current biosynthesis arrays can synthesize biomolecules in a matter of hours. 3D structure of the nanopore array biosynthesis systems described herein provide parallel nanopore channel array systems, which can further miniaturize a microarray into a nanopore array with further reduction in size and increasing compaction. Decreasing the system size also reduces the requirement for the amount of sample and reagents needed, and decreases the system operating cost, resulting in a more efficient and affordable portable biomolecular synthesis platform.

ADDITIONAL ASPECTS

In addition to the claimed invention and by way of non-limiting examples, further embodiments or aspects of the invention are described herein.

1. A method of synthesizing a plurality of different oligonucleotides using a nanofluidic array comprising a plurality of nanopore channels, a plurality of electrodes, and an electrolyte solution in the plurality of nanopore channel and in electrical contact with the plurality of electrodes, the method comprising:
   a. coupling first and second primers to respective inner walls of first and second nanopore channels of the plurality of nanopore channels, the first and second primers each having a protecting group;
   b. applying a voltage to a first electrode of the plurality of electrodes that corresponds to the first nanopore channel to produce an acid from the electrolyte solution at the first electrode, wherein the first electrode comprises a first anode and a first cathode disposed at opposite sides of the first nanopore channel, while not applying a voltage to a second electrode of the plurality of electrodes that corresponds to the second nanopore channel;
   c. the acid removing the protecting group from the first primer;
   d. coupling a first nucleotide to the first primer with the protecting group removed to form a first intermediate product;
   e. repeating steps b. to d. on the first intermediate product and/or the second primer until the plurality of different oligonucleotides is synthesized.

2. A nanopore device for synthesizing an oligonucleotide, comprising:
   a plurality of independently addressable electrodes defining a plurality of nanopore channels,
   wherein the plurality of independently addressable electrodes form an array, such that each nanopore channel of the plurality of nanopore channels is independently addressable;
   a pump to move fluid into and out of the plurality of nanopore channels; and
   a processor operatively coupled to the plurality of independently addressable electrodes, and the pump,
   wherein the processor is programmed to instruct the plurality of independently addressable electrodes, and the pump to perform a method, the method comprising
   a. pumping a primer into a nanopore channel of the plurality of nanopore channels, the primer having a protecting group, to couple the primer to an inner wall of nanopore channel;
   b. applying a voltage to an electrode of the plurality of independently addressable electrodes, to produce an acid from the electrolyte solution at the electrode;
   c. the acid removing the protecting group from the primer;
   d. pumping a nucleotide into the nanopore channel to couple the nucleotide to the primer with the protecting group removed to form an intermediate product;
   e. repeating steps b. to d. on the intermediate product until the oligonucleotide is synthesized.

3. The device of aspect 2, wherein the electrode comprises an anode and a cathode disposed at opposite sides of the nanopore channel.

4. The device of aspect 3, wherein the anode and the cathode are disposed at opposite ends of a longitudinal axis of the nanopore channel.

5. The device of aspect 3, wherein the anode and the cathode are disposed at opposite sides of the nanopore channel along a longitudinal axis of the nanopore channel.

6. The device of aspect 3, wherein the plurality of independently addressable electrodes defining the plurality of nanopore channels is contained in a fluidic or MEMS device.

7. The device of aspect 3, wherein the nanopore device is a 3D nanopore device.

8. The device of aspect 3, wherein the processor is programmed to instruct the plurality of independently addressable electrodes, and the pump to perform a method for synthesizing DNA, RNA, polypeptides, or aptamers.

9. The device of aspect 3, wherein each nanopore channel of the plurality of nanopore channels is independently addressable by a respective electrode of the plurality of independently addressable electrodes.

10. A method of synthesizing an oligonucleotide using a microfluidic device comprising a plurality of microchannels, a plurality of electrodes, and an electrolyte solution in the plurality of microchannel and in electrical contact with the plurality of electrodes, the method comprising:
   a. coupling a primer to an inner wall of a microchannel of the plurality of microchannels, the primer having a protecting group;

b. applying a voltage to an electrode of the plurality of electrodes that corresponds to the microchannel to produce an acid from the electrolyte solution at the electrode, wherein the electrode comprises an anode and a cathode disposed at opposite sides of the microchannel;

c. the acid removing the protecting group from the primer;

d. coupling a nucleotide to the primer with the protecting group removed to form an intermediate product;

e. repeating steps b. to d. on the intermediate product until the oligonucleotide is synthesized.

11. A method of synthesizing an oligonucleotide using a MEMS-based array device comprising a plurality of channels, a plurality of electrodes, and an electrolyte solution in the plurality of channel and in electrical contact with the plurality of electrodes, the method comprising:

a. coupling a primer to an inner wall of a channel of the plurality of channels, the primer having a protecting group;

b. applying a voltage to an electrode of the plurality of electrodes that corresponds to the channel to produce an acid from the electrolyte solution at the electrode, wherein the electrode comprises an anode and a cathode disposed at opposite sides of the channel;

c. the acid removing the protecting group from the primer;

d. coupling a nucleotide to the primer with the protecting group removed to form an intermediate product;

e. repeating steps b. to d. on the intermediate product until the oligonucleotide is synthesized.

While specific nanoelectrode addressing configurations and electrical control schemes are disclosed herein, other nanoelectrode addressing configurations and electrical control schemes can be used with the disclosed embodiments without departing from the spirit and scope of the inventions. While the systems and methods described herein involve synthesis of biopolymers such as oligonucleotides (e.g., DNA and RNA), oligopeptides, and oligosaccharides, the systems and methods can also be used to generate other chain polymers and/or for click chemistry. While the systems and methods described herein utilize a 3D nanopore array, the principles of the systems and methods are also applicable to other types of biosynthesis systems. Embodiments are not limited to nanopore arrays but also include larger pore sized array structures such as microarrays (pore size larger than 1000 nm) and MEMS-based arrays.

The corresponding structures, materials, acts and equivalents of all means or step plus function elements in the claims below are intended to include any structures, materials, acts and equivalents for performing the function in combination with other claimed elements as specifically claimed. It is to be understood that while the invention has been described in conjunction with the above embodiments, the foregoing description and claims are not to limit the scope of the invention. Other aspects, advantages and modifications within the scope to the invention will be apparent to those skilled in the art to which the invention pertains.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. Other details of the present invention, these may be appreciated in connection with the above-referenced patents and publications as well as generally known or appreciated by those with skill in the art. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A method of synthesizing an oligonucleotide using a nanofluidic device comprising a plurality of nanopore channels, a plurality of electrodes, and an electrolyte solution in the plurality of nanopore channel and in electrical contact with the plurality of electrodes, the method comprising:
    [a] coupling a primer to an inner wall of a nanopore channel of the plurality of nanopore channels, the primer having a protecting group;
    [b] applying a voltage to an electrode of the plurality of electrodes that corresponds to the nanopore channel to produce an acid from the electrolyte solution at the electrode, wherein the electrode comprises an anode and a cathode disposed at opposite sides of the nanopore channel;
    [c] the acid removing the protecting group from the primer;
    [d] coupling a nucleotide to the primer with the protecting group removed to form an intermediate product;
    [e] repeating steps [b] to [d] on the intermediate product until the oligonucleotide is synthesized.

2. The method of claim 1, wherein coupling the primer to the inner wall of the nanopore channel comprises coupling a dress polymer to the inner wall of the nanopore channel and couple the primer to the dress polymer.

3. The method of claim 2, wherein the dress polymer is selected from the group consisting of polyethylene glycol (PEG 5000) monomethyl ester, poly(ortho esters), aliphatic polyester, temperature resistant polymers, aliphatic homopolymers, polycaprolactons, polymers with cosolvents, b polar polymers, hydrophilic polymers, and hydrophobic polymers.

4. The method of claim 1, wherein the protecting group comprises dimethoxytrityl ("DMT").

5. The method of claim 1, wherein the electrolyte solution comprises hydroquinone, benzoquinone, and acetonitrile,
    wherein applying the voltage to the electrode produces the acid at the anode by oxidation of the
    wherein applying the voltage to the electrode generates the hydroquinone at the cathode by reduction of the benzoquinone,
    wherein the generated acid travels from the anode to the cathode through the nanopore channel, and
    wherein applying the voltage to the electrode increases a rate of flow of the generated acid through the nanopore channel.

6. The method of claim 1, wherein the nucleotide comprises a phosphoramidite monomer,
    wherein coupling the phosphoramidite monomer to the primer with the protecting group removed comprises activating the phosphoramidite monomer with an azole, and
    wherein the azole is selected from the group consisting of tetrazole, 2-ethylthiotetrazole, 2-benzylthiotetrazole, and 4,5-dicyanoim idazole.

7. The method of claim 1, further comprising stabilizing the intermediate product before step [e].

8. The method of claim 7, wherein stabilizing the intermediate product comprises oxidizing a phosphite triester to a phosphate triester, the method further comprising oxidizing the phosphite triester to the phosphate triester with a solution of iodine and pyridine.

9. The method of claim 1, further comprising capping an unreacted 5'-OH, wherein capping the unreacted 5'-OH comprises reacting the unreacted 5'-OH with acetic anhydride and N-methylimidazole in tetrahydrofuran.

10. The method of claim 1, wherein repeating steps [b] to [d] on the intermediate product comprising coupling a different nucleotide to the intermediate product.

11. The method of claim 1, further comprising synthesizing a second oligonucleotide in a second nanopore channel of the nanofluidic device using steps [a] to e.

12. The method of claim 11, wherein the second oligonucleotide is different from the oligonucleotide.

13. The method of claim 1, further comprising a primary product interacting with the electrolyte solution to generate a secondary product.

14. The method of claim 1, wherein the plurality of electrodes and the plurality of nanopore channels are contained in a fluidic or MEMS system.

15. The method of claim 1, wherein a size of the nanopore channel and an efficiency of producing the acid increase an efficiency of the method of synthesizing the oligonucleotide.

16. The method of claim 1, further comprising synthesizing identical oligonucleotides in all nanopore channels of the plurality of nanopore channels.

17. The method of claim 16, wherein the voltage is applied to all electrodes of the plurality of electrodes as a pulse with an amount of current.

18. The method of claim 17, wherein the voltage is applied to all electrodes of the plurality of electrodes as a plurality of pulses with the amount of current.

19. The method of claim 1, wherein the voltage is applied to the electrode in a stepwise manner.

20. The method of claim 1, further comprising varying the voltage applied to the electrode to vary the amount of acid produced from the electrolyte solution at the electrode.

* * * * *